United States Patent
Luo et al.

(10) Patent No.: US 11,819,336 B2
(45) Date of Patent: Nov. 21, 2023

(54) ANESTHESIA STAGE IDENTIFICATION AND ANESTHESIA DEPTH CALCULATION METHOD AND DEVICE

(71) Applicant: SHENZHEN MINDRAY BIO-MEDICAL ELECTRONICS CO., LTD., Shenzhen (CN)

(72) Inventors: Hanyuan Luo, Shenzhen (CN); Xingliang Jin, Shenzhen (CN); Xianliang He, Shenzhen (CN); Zhigang Ye, Shenzhen (CN); Ningling Zhang, Shenzhen (CN); Ming Li, Shenzhen (CN); Zuming Yao, Shenzhen (CN)

(73) Assignee: SHENZHEN MINDRAY BIO-MEDICAELECTRONICS CO., LTD., Shenzhen (CN)

( * ) Notice: Subject to any disclaimer, the term of this patent is extended or adjusted under 35 U.S.C. 154(b) by 391 days.

(21) Appl. No.: 16/909,964

(22) Filed: Jun. 23, 2020

(65) Prior Publication Data

US 2020/0315525 A1    Oct. 8, 2020

Related U.S. Application Data

(63) Continuation of application No. PCT/CN2017/120346, filed on Dec. 29, 2017.

(51) Int. Cl.
*A61B 5/316* (2021.01)
*A61B 5/00* (2006.01)
*A61B 5/374* (2021.01)

(52) U.S. Cl.
CPC ........... *A61B 5/4821* (2013.01); *A61B 5/316* (2021.01); *A61B 5/374* (2021.01); *A61B 5/7246* (2013.01)

(58) Field of Classification Search
CPC ....... A61B 5/316; A61B 5/374; A61B 5/4821; A61B 5/7246
See application file for complete search history.

(56) References Cited

U.S. PATENT DOCUMENTS

2002/0019588 A1* 2/2002 Marro .................. A61B 5/4821
600/383
2003/0055355 A1* 3/2003 Viertio-Oja .......... A61B 5/1106
600/544

(Continued)

FOREIGN PATENT DOCUMENTS

CN    202821345 U    3/2013
CN    103637798 A    3/2014

(Continued)

OTHER PUBLICATIONS

International Search Report issued in corresponding International Application No. PCT/CN2017/120346, dated Aug. 30, 2018, 4 pages.

*Primary Examiner* — Eileen M Adams
(74) *Attorney, Agent, or Firm* — BAYES PLLC

(57) ABSTRACT

An anesthesia stage identification method for identifying an anesthesia stage at which a patient is located is disclosed. The method includes collecting an electroencephalogram signal, calculating at least two characteristics of the collected electroencephalogram signal according to a preset frequency, and determining the anesthesia stage at which the patient is located in a corresponding time period according to the at least two calculated characteristics. The identification method can accurately determine the anesthesia stage, and resolve the problems of abnormal falling during a lucid interval and slow response speed during an induction stage caused by misjudgment.

17 Claims, 6 Drawing Sheets

(56) References Cited

U.S. PATENT DOCUMENTS

| | | | |
|---|---|---|---|
| 2005/0043652 A1* | 2/2005 | Lovett | A61B 5/1116 600/595 |
| 2005/0137494 A1* | 6/2005 | Viertio-Oja | A61B 5/7203 600/544 |
| 2007/0010795 A1* | 1/2007 | Sarkela | A61B 5/389 604/503 |
| 2008/0294217 A1* | 11/2008 | Lian | G06K 9/00496 600/301 |
| 2011/0118620 A1 | 5/2011 | Scheib | |
| 2012/0231838 A1* | 9/2012 | Lyon | G11B 19/02 455/567 |
| 2016/0081617 A1* | 3/2016 | Iyer | A61B 5/6814 600/544 |
| 2017/0196501 A1* | 7/2017 | Watson | A61B 5/7221 |
| 2017/0281030 A1* | 10/2017 | Jin | A61B 5/4088 |
| 2018/0000409 A1* | 1/2018 | Jensen | A61B 5/352 |

FOREIGN PATENT DOCUMENTS

| | | | |
|---|---|---|---|
| CN | 104545949 A | 4/2015 | |
| CN | 104644166 A | 5/2015 | |

\* cited by examiner

ANESTHESIA STAGE IDENTIFICATION AND ANESTHESIA DEPTH CALCULATION METHOD AND DEVICE

CROSS-REFERENCE TO RELATED APPLICATION

This application is a continuation of PCT Application No. PCT/CN2017/120346, filed Dec. 29, 2017, entitled "ANESTHESIA STAGE IDENTIFICATION AND ANESTHESIA DEPTH CALCULATION METHOD AND DEVICE," the entire contents of which are incorporated herein by reference.

TECHNICAL FIELD

This disclosure relates to the field of anesthesia electroencephalogram monitoring, and in particular to an anesthesia stage identification and anesthesia depth calculation method and device based on an electroencephalogram.

BACKGROUND

Anesthesia refers to the use of a drug or other methods to make a patient in whole or in part lose the sensation temporarily to achieve the purpose of painlessness, so as to perform surgical treatment. In surgical operations, the role of anesthesia is extremely important.

Proper anesthesia enables patients to undergo surgical treatment without pain, thereby saving the patients from pain while facilitating the normal operation of doctors. However, improper anesthesia cannot eliminate the patients' pain, but brings a series of other problems. For example, if the anesthesia is too deep, the function of the nervous system of the patient may be damaged, and neurological sequelae may occur. If the anesthesia is too shallow, it is possible that a transitional reaction of the body caused by noxious stimuli cannot be suppressed, so that the patient suffers from intraoperative awareness, causing the patient to have intraoperative memory, which may cause serious mental or sleep disorders. Therefore, the monitoring of an anesthesia stage is very important.

However, in the prior art, there are some problems in the determination of the anesthesia stage. As shown in FIG. 1, when the anesthesia depth value is between 80 and 100, the patient is in an alert stage, and when the anesthesia depth value is between 40 and 60, the patient is in an anesthesia stage. In a segment M of a lucid interval, there was an abnormal falling in the anesthesia depth, so that the patient is mistakenly determined to be in the anesthesia stage. After an anesthesia drug is delivered to the patient for a long period of time, the anesthesia depth value of the patient should show a decreasing trend at a start point of a segment N, but is still at an alert level during the segment N, making the overall rate of decrease in anesthesia depth become slower.

The above-mentioned problems occur because eye-closed eye movement signals in the alert stage and electroencephalogram signals in an anesthesia induction stage may be highly similar, and misjudgment between the two is likely to occur. That is, when the patient is in the alert stage, an eye movement signal will be generated. When the eye movement signal is mistakenly identified as an electroencephalogram signal, the anesthesia depth value will fall abnormally. When the anesthesia drug starts to work, the brain will produce an electroencephalogram signal similar to the eye movement signal. At this time, the patient is already in the anesthesia stage, but the electroencephalogram signal may be mistakenly identified as the eye movement signal. As a result, the anesthesia depth value is still maintained at the level of alert stage, and the patient is mistakenly determined to be in the alert stage.

SUMMARY

This disclosure is proposed in view of the above circumstances, and objects thereof are to provide an anesthesia stage identification method and an anesthesia depth calculation method, which can accurately determine the anesthesia stage, and resolves the problems of abnormal falling during a lucid interval and slow response speed during an induction stage caused by misjudgment.

To this end, an aspect of this disclosure provides an anesthesia stage identification method for identifying an anesthesia stage at which a patient may be located. The method may include collecting an electroencephalogram signal; calculating at least two characteristics of the collected electroencephalogram signal according to a preset frequency; and determining the anesthesia stage at which the patient may be located in a corresponding time period according to the at least two calculated characteristics.

In this disclosure, by calculating at least two characteristics of the collected electroencephalogram signal according to a preset frequency, the anesthesia stage of the patient corresponding to the collected electroencephalogram signal may be determined. In this case, it is possible to resolve the problems of abnormal falling during a lucid interval and slow response speed during an induction stage caused by misjudgment, and to accurately obtain the anesthesia stage at which the patient may be located.

In the anesthesia stage identification method according to the aspect of this disclosure, the collected electroencephalogram signal may include electroencephalogram signals of at least two channels; and the at least two characteristics of the electroencephalogram signal may include a correlation between the electroencephalogram signals of any two of the channels, and a high-frequency energy in the electroencephalogram signal of any one of the channels. As a result, the anesthesia stage at which the patient may be located may be accurately obtained according to the high-frequency energy and the correlation.

In the anesthesia stage identification method according to the aspect of this disclosure, the step of determining the anesthesia stage at which the patient may be located in the corresponding time period according to the at least two calculated characteristics may include: determining the anesthesia stage at which the patient may be located in the corresponding time period from the obtained high-frequency energy, and the correlation between the electroencephalogram signals of any two of the channels or changes in the correlation. As a result, the anesthesia stage at which the patient may be located can be obtained more accurately according to the high-frequency energy and the correlation or changes in the correlation.

In the anesthesia stage identification method according to the aspect of this disclosure, the anesthesia stage may be divided into: a lucid interval, an induction stage, a stable stage and a recovery stage. As a result, which one of the lucid interval, the induction stage, the stable stage and the recovery stage in which the patient may be located can be obtained more accurately according to the high-frequency energy and the correlation or changes in the correlation.

In the anesthesia stage identification method according to the aspect of this disclosure, the high-frequency energy may be compared with a first threshold to determine whether the high-frequency energy is high or low. As a result, the anesthesia stage at which the patient may be located can be determined depending on whether the high-frequency energy is high or low.

In the anesthesia stage identification method according to the aspect of this disclosure, the first threshold may be an adaptive threshold related to the high-frequency energy. As a result, whether the high-frequency energy is high or low can be accurately obtained, and the anesthesia stage at which the patient may be located can be determined more accurately.

In the anesthesia stage identification method according to the aspect of this disclosure, if the high-frequency energy is high and the correlation is negative, the anesthesia stage may be determined to be the lucid interval; if the high-frequency energy is low and the correlation is positive, the anesthesia stage may be determined to be the stable stage; if the patient is in the lucid interval, as the high-frequency energy changes from high to low, and the correlation is positive, the patient may be determined to enter the induction stage; and if the patient is in the stable stage, as the high-frequency energy changes from low to high, and the correlation is negative, the patient may be determined to enter the recovery stage. As a result, the anesthesia stage at which the patient may be located can be accurately obtained according to the comprehensive determination of the high-frequency energy and the correlation.

In the anesthesia stage identification method according to the aspect of this disclosure, the correlation may be calibrated by a Pearson correlation coefficient. As a result, the correlation between the electroencephalogram signals can be obtained, and the anesthesia stage at which the patient may be located can be further obtained according to the correlation.

In the anesthesia stage identification method according to the aspect of this disclosure, if the Pearson correlation coefficient is greater than or equal to a second threshold, the correlation may be determined to be a positive correlation; and if the Pearson correlation coefficient is less than or equal to a third threshold, the correlation may be determined to be a negative correlation. As a result, the anesthesia stage can be determined more accurately.

A further aspect of this disclosure provides an anesthesia depth calculation method, may include: collecting an electroencephalogram signal; acquire an anesthesia stage at which a patient is located; determining an anesthesia depth calculation strategy according to the anesthesia stage at which the patient may be located; and calculating an anesthesia depth in a corresponding time period according to the determined anesthesia depth calculation strategy.

In this disclosure, different anesthesia depth calculation strategies may be used according to different anesthesia stages, to obtain the anesthesia depth corresponding to the collected electroencephalogram signal. In this case, the anesthesia depth value can be obtained more accurately and quickly.

In the anesthesia depth calculation method according to the further aspect of this disclosure, the anesthesia depth calculation strategy includes at least a first calculation strategy and a second calculation strategy. As a result, the anesthesia depth value can be obtained according to different calculation strategies.

In the anesthesia depth calculation method according to the further aspect of this disclosure, a response speed at which the anesthesia depth may be calculated by using the first calculation strategy may be faster than a response speed at which the anesthesia depth may be calculated by using the second calculation strategy; and the step of calculating the anesthesia depth in the corresponding time period according to the determined anesthesia depth calculation strategy may include: using the first calculation strategy when the patient may be in the induction stage. As a result, a faster anesthesia depth response speed can be obtained.

In the anesthesia depth calculation method according to the further aspect of this disclosure, the first calculation strategy may be to calculate the anesthesia depth with a relatively short signal, and the second calculation strategy may be to calculate the anesthesia depth with a longer signal than in the first calculation strategy. As a result, the response speed at which the anesthesia depth may be calculated by using the first calculation strategy may be faster than the response speed at which the anesthesia depth may be calculated by using the second calculation strategy.

In the anesthesia depth calculation method according to the further aspect of this disclosure, the step of calculating the anesthesia depth in the corresponding time period according to the determined anesthesia depth calculation strategy may include: using the first calculation strategy and the second calculation strategy to calculate the anesthesia depth in parallel; and setting, when the patient may be in the induction stage, the calculation result of the first calculation strategy as the anesthesia depth at the corresponding stage. As a result, it is possible to respond to the anesthesia depth more quickly.

In the anesthesia depth calculation method according to the further aspect of this disclosure, the step of acquiring the anesthesia stage at which the patient is located may include: using the collected electroencephalogram signal to calculate at least two characteristics of the electroencephalogram signal; and determining the anesthesia stage at which the patient may be located in the corresponding time period according to the two characteristics. As a result, the anesthesia stage at which the patient may be located can be obtained more efficiently.

A still further aspect of this disclosure provides an anesthesia depth calculation device, may include: a collection module for collecting an electroencephalogram signal; a determination module for acquiring an anesthesia stage at which a patient may be located; a selection module for determining an anesthesia depth calculation strategy according to the anesthesia stage at which the patient may be located; and a calculation module for calculating an anesthesia depth in a corresponding time period according to the determined anesthesia depth calculation strategy. As a result, the anesthesia depth value can be obtained more accurately and quickly.

In the anesthesia depth calculation device according to the still further aspect of this disclosure, the anesthesia depth calculation strategy may include at least a first calculation strategy and a second calculation strategy, the first calculation strategy may be to calculate the anesthesia depth with a relatively short signal, and the second calculation strategy may be to calculate the anesthesia depth with a longer signal than in the first calculation strategy. The anesthesia depth value obtained by using the second calculation strategy may be more stable than the anesthesia depth value obtained by the first calculation strategy, and at the same time, the anesthesia depth value obtained by using the first calculation strategy may be more sensitive than the anesthesia depth value obtained by the second calculation strategy. In this case, different calculation strategies can be adjusted at different anesthesia stages, so as to obtain different calculation strategies for the outgoing value at different anesthesia stages, to meet the clinical requirements for different anesthesia stages.

A yet further aspect of this disclosure may provide an anesthesia depth calculation device, may include: a sensor for collecting an electroencephalogram signal; a memory for storing the collected electroencephalogram signal; and a processor for performing the following steps: calculating at least two characteristics of the collected electroencephalogram signal according to a preset frequency; and determining the anesthesia stage at which the patient may be located in a corresponding time period according to the at least two calculated characteristics. In this case, it is possible to resolve the problems of abnormal falling during a lucid interval and slow response speed during an induction stage caused by misjudgment, and to accurately obtain the anesthesia stage at which the patient is located.

In the anesthesia depth calculation device according to the yet further aspect of this disclosure, the collected electroencephalogram signal may includes electroencephalogram signals of at least two channels; and the at least two characteristics of the electroencephalogram signal may include a correlation between the electroencephalogram signals of any two of the channels, and a high-frequency energy in the electroencephalogram signal of any one of the channels. As a result, the anesthesia stage at which the patient may be located can be accurately obtained according to the high-frequency energy and the correlation.

In the anesthesia depth calculation device according to the yet further aspect of this disclosure, the high-frequency energy may be compared with a first threshold to determine whether the high-frequency energy is high or low. As a result, the anesthesia stage at which the patient may be located can be determined depending on whether the high-frequency energy is high or low.

In the anesthesia depth calculation device according to the yet further aspect of this disclosure, the first threshold may be an adaptive threshold related to the high-frequency energy. As a result, whether the high-frequency energy is high or low can be accurately obtained, and the anesthesia stage at which the patient may be located can be determined more accurately.

In the anesthesia depth calculation device according to the yet further aspect of this disclosure, the correlation may be calibrated by a Pearson correlation coefficient. As a result, the correlation between the electroencephalogram signals can be obtained, and the anesthesia stage at which the patient may be located can be further obtained according to the correlation.

In the anesthesia depth calculation device according to the yet further aspect of this disclosure, the processor may be further used to perform the following steps: determining an anesthesia depth calculation strategy according to the anesthesia stage at which the patient is located; and calculating an anesthesia depth in a corresponding time period according to the determined anesthesia depth calculation strategy. In this case, the anesthesia depth value can be obtained more accurately and quickly.

According to this disclosure, it is possible to provide an anesthesia stage identification and anesthesia depth calculation method and device based on an electroencephalogram, which can accurately determine the anesthesia stage, and resolves the problems of abnormal falling during a lucid interval and slow response speed during an induction stage caused by misjudgment.

DETAILED DESCRIPTION OF EMBODIMENTS

Figure 1:
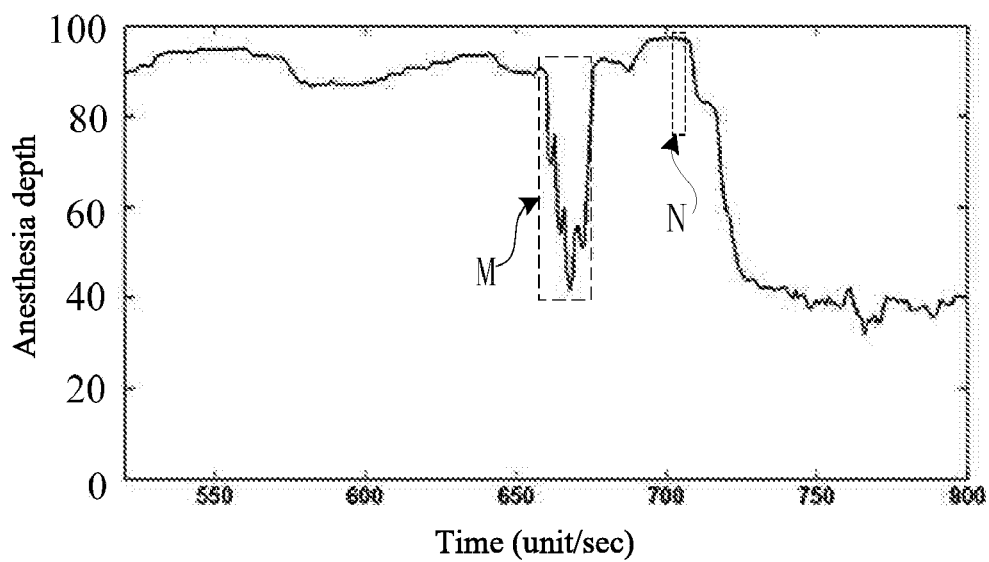
FIG. 1 is a schematic diagram showing the problems in the existing anesthesia stage identification techniques.

Preferred embodiments of this disclosure may be described below in detail with reference to the accompanying drawings. In the following description, the same components may be provided with the same reference numerals. Repeated description may be omitted. In addition, the accompanying drawings may be schematic figures. The proportions among the sizes of the components, the shapes of the components, and the like may be different from those in reality.

Figure 2A:
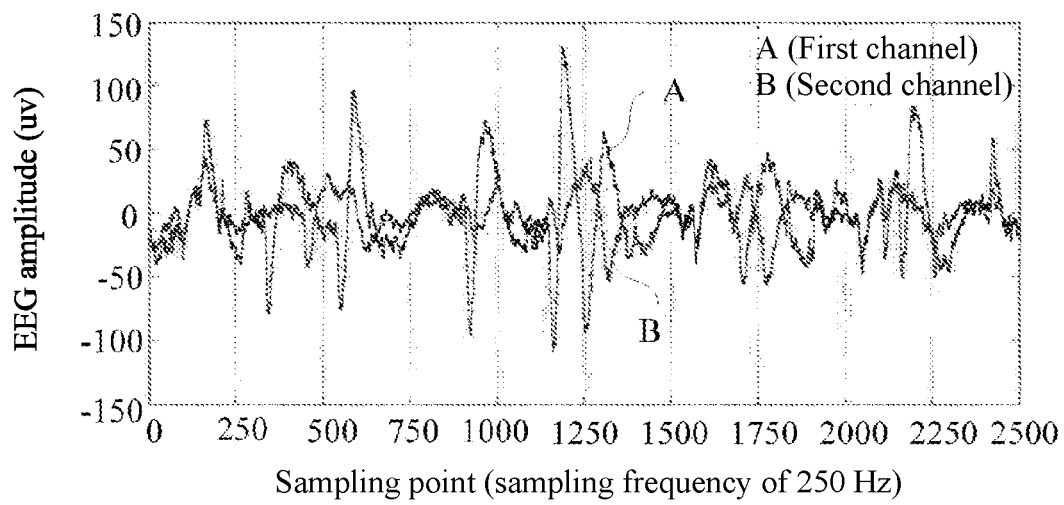
FIG. 2a is a schematic diagram showing waveforms of eye-closed eye movement signals in an alert stage according to an embodiment of this disclosure.
Figure 2B:
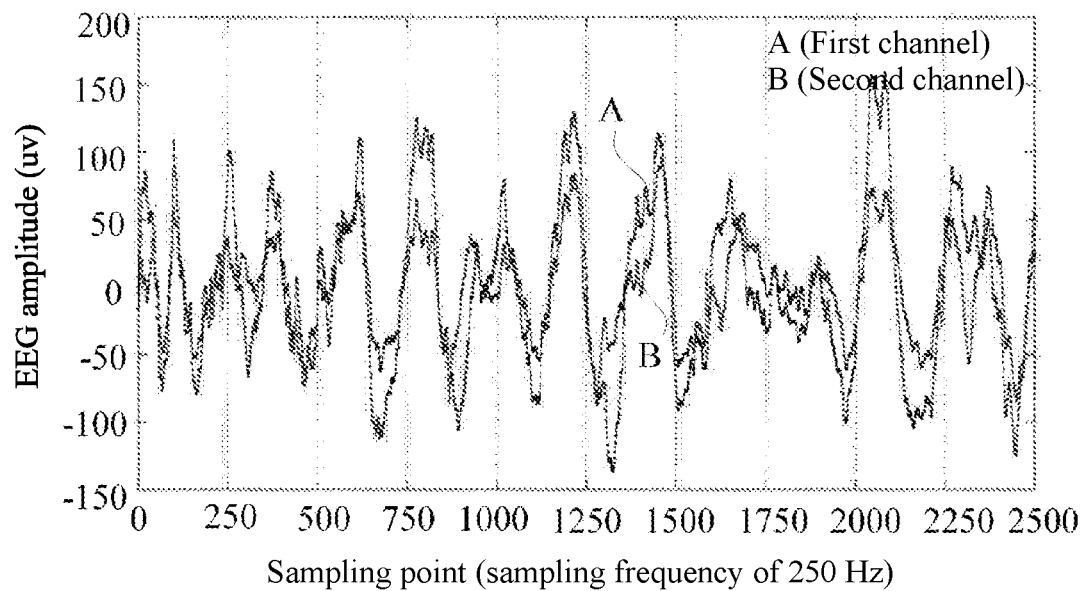
FIG. 2b is a schematic diagram showing waveforms of electroencephalogram signals in an anesthesia induction stage according to an embodiment of this disclosure.
Figure 3:
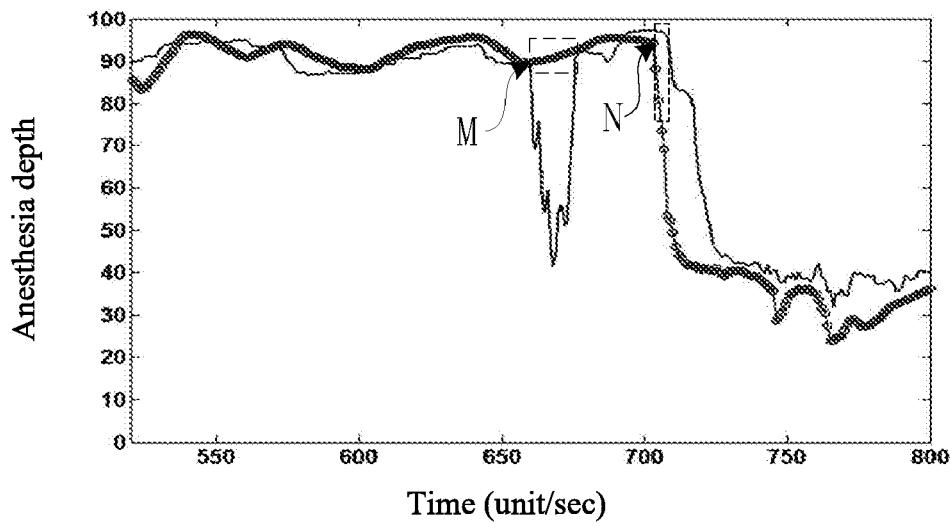
FIG. 3 is a schematic diagram showing the effect of an anesthesia stage identification technique according to an embodiment of this disclosure.
Figure 4:
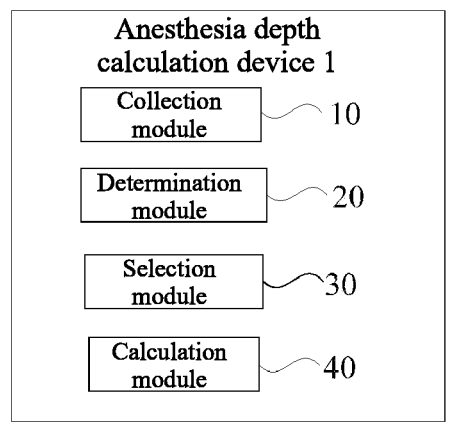
FIG. 4 is a block diagram showing modules of an anesthesia depth calculation device according to an embodiment of this disclosure.

FIG. 2a may be a schematic diagram showing waveforms of eye-closed eye movement signals in an alert stage according to an embodiment. FIG. 2b may be a schematic diagram showing waveforms of electroencephalogram signals in an anesthesia induction stage according to an embodiment. FIG. 3 may be a schematic diagram showing the effect of an anesthesia stage identification technique according to an embodiment. FIG. 4 may be a block diagram showing modules of an anesthesia depth calculation device according to an embodiment.

In one embodiment, as shown in FIG. 4, the anesthesia depth calculation device 1 may include a collection module 10, a determination module 20, a selection module 30 and a calculation module 40.

In one embodiment, the collection module 10 may collect, for example, an electroencephalogram signal from an organism. The electroencephalogram signal is an important bioelectrical signal of an organism (such as a human or an animal), and is the overall reflection of the electrical activity of cerebral nerve cells in the cerebral cortex. The electroencephalogram signal may be closely related to the anesthesia stage. The electroencephalogram signals at different anesthesia stages may have different characteristics in different aspects such as time domain and frequency domain.

By analyzing the electroencephalogram signals from different aspects, the corresponding anesthesia stage can be obtained.

In one embodiment, the collection module 10 may be a sensor. That is, the electroencephalogram signal may be collected by means of a sensor. For example, the electroencephalogram signal may be collected by means of electrode pads. In addition, it may also be obtained by means of other electroencephalogram signal collection devices.

For the collection of the electroencephalogram signal, generally, in order to improve the accuracy of the determination of the anesthesia stage, electroencephalogram signals of multiple channels may be often collected. In some examples, the electroencephalogram signals of the multiple channels may be collected by means of multiple electrode pads. For example, electroencephalogram signals of two channels may be collected by means of three electrode pads. Specifically, signals may be collected by means of three electrode pads, one of which may be a common electrode pad, namely, an R electrode pad, and the other two electrode pads may be a T electrode pad and an E electrode pad. The electroencephalogram signals of the two channels can be obtained by means of the potential differences between the T and E electrode pads and the R electrode pad, respectively.

In one embodiment, the electroencephalogram signal may include a physiological interference signal such as an electromyogram interference signal. The electromyogram interference signal may be located in the high-frequency part of the electroencephalogram signal.

In one embodiment, the high-frequency energy may be different at different anesthesia stages. For example, the high-frequency energy in a lucid interval may be relatively high, and the high-frequency energy in an anesthesia period may be relatively low. As a result, the electromyogram interference signal in the electroencephalogram signal can be extracted, and different anesthesia stages can be determined depending on whether the high-frequency energy is high or low (also referred to as whether the electromyogram level is high or low).

In one embodiment, as described above, the collection module 10 may collect electroencephalogram signals of multiple channels. That is, the collection module 10 may collect electroencephalogram signals of at least two channels. Specifically, when collecting electroencephalogram signals, at least two different positions of the head of a patient may be selected to collect the electroencephalogram signals. For example, when collecting electroencephalogram signals of three channels, it is possible to select an area around the human eye to collect an electroencephalogram signal, to select an area where the brain of the patient may be located to collect an electroencephalogram signal, and to select an area around an ear of the patient to collect an electroencephalogram signal.

In some examples, the collection module 10 may collect electroencephalogram signals of two channels. As an example of electroencephalogram signals of two channels, the electroencephalogram signal of a first channel such as an RT channel may include an eye movement interference signal, and the electroencephalogram signal of a second channel such as an RE channel do not include any eye movement interference signal. At different anesthesia stages, the waveform of the electroencephalogram signal of the first channel and the waveform of the electroencephalogram signal of the second channel may have different characteristics.

For example, in the lucid interval, if the patient blinks, the waveform of the electroencephalogram signal of the first channel and the waveform of the electroencephalogram signal of the second channel may be in opposite directions, that is, the electroencephalogram signal of the first channel and the electroencephalogram signal of the second channel may be negatively correlated. In an induction stage, the waveform of the electroencephalogram signal of the first channel and the waveform of the electroencephalogram signal of the second channel may be in the same direction, that is, the electroencephalogram signal of the first channel and the electroencephalogram signal of the second channel may be positively correlated. As a result, the anesthesia stage at which the patient may be located can be determined according to the correlation between the electroencephalogram signal of the first channel and the electroencephalogram signal of the second channel.

Furthermore, the collection module 10 may also collect electroencephalogram signals of more than three channels. In addition, the collection mode of the collection module 10 may be adopted in different areas, with one channel being selected in each area, or may be adopted in the same area where multiple channels may be selected.

In addition, in one embodiment, the anesthesia depth calculation device 1 may further include a memory (not shown). The memory may be used to store the collected electroencephalogram signal. In some examples, the memory may be connected to the collection module 10, in which case, the electroencephalogram signal collected by the collection module 10 may be stored in the memory.

In one embodiment, as shown in FIG. 4, the anesthesia depth calculation device 1 may further include a determination module 20. The determination module 20 may be used to acquire the anesthesia stage at which the patient may be located. Specifically, the determination module 20 may receive the electroencephalogram signal collected by the collection module 10 and acquire the anesthesia stage at which the patient may be located based on the electroencephalogram signal. In some examples, the determination module 20 may be a processor such as a central processing unit (CPU), a microprocessor unit (MPU), or an application specific integrated circuit (ASIC).

In one embodiment, the determination module 20 may use the collected electroencephalogram signal to calculate at least two characteristics of the collected electroencephalogram signal according to a preset frequency; and determine the anesthesia stage at which the patient may be located in a corresponding time period according to the at least two calculated characteristics. That is, the determination module 20 may automatically identify, according to the collected electroencephalogram signal, the anesthesia stage at which the patient may be located in the case of the corresponding electroencephalogram signal.

In one embodiment, the at least two characteristics of the electroencephalogram signal may be a correlation between the electroencephalogram signals of any two of the channels, and a high-frequency energy in the electroencephalogram signal of any one of the channels. The high-frequency energy may be the energy of the electroencephalogram signal in a frequency band above 30 Hz, which can reflect the electromyogram (EMG) level to a certain extent. As a result, the determination module 20 can determine the anesthesia stage at which the patient may be located in the corresponding time period from the obtained high-frequency energy, and the correlation between the electroencephalogram signals of any two of the channels or changes in the correlation.

In one embodiment, the determination module 20 may include an energy calculation unit. The energy calculation unit may extract the electromyogram interference signal from the collected electroencephalogram signal by means of the high-frequency energy. Electromyogram interference signals in electroencephalogram signals may be mainly distributed in a frequency-domain band of 50 to 300 Hz, that is, the electromyogram interference signals may be in a high-frequency band of the electroencephalogram signals.

In one embodiment, the high-frequency energy may be different under different anesthesia stage conditions. The energy calculation unit may calculate the extracted electromyogram interference signal to obtain the high-frequency energy.

In one embodiment, the level of the high-frequency energy of the electromyogram interference signal may be quantified using a power spectral density. The power spectral density may be calculated by means of the following steps:

first, performing a Fourier transform on the electromyogram interference signal by means of a Fourier transform (1), $$X(\omega) = F[f(t)] = \int_{-\infty}^{\infty} f(t)e^{-i\omega t} dt \quad (1)$$

and then, using, according to the Parseval's theorem, the sum of the square of the Fourier transform to obtain the power spectral density. Formula (2) is the formula of Parseval's theorem.

$$\int_{-\infty}^{\infty} |x(t)|^2 dt = \int_{-\infty}^{\infty} |x(\omega)|^2 d\omega \quad (2)$$

In one embodiment, the high-frequency energy can be obtained by using the above calculation method. Different anesthesia stages may be determined depending on whether the high-frequency energy is high or low.

In one embodiment, the determination module 20 may further include a correlation calculation unit.

In one embodiment, the correlation calculation unit may select two channels from the multiple channels. For the electroencephalogram signals in two channels, the first electroencephalogram signal may include an eye movement interference signal, and the second electroencephalogram signal does not include any eye movement interference signal.

In one embodiment, under different anesthesia stage conditions, the waveform of the first electroencephalogram signal and the waveform of the second electroencephalogram signal may have different characteristics. The correlation calculation unit may calculate the correlation between the first electroencephalogram signal and the second electroencephalogram signal. The correlation between the electroencephalogram signals may be a time-domain correlation, or a frequency-domain correlation.

In one embodiment, the calculation of the correlation may be obtained by means of a Pearson correlation coefficient. The Pearson correlation coefficient may be used to measure the linear relationship between the electroencephalogram signals in the two channels. The Pearson correlation coefficient may be expressed by r, and its definition expression is:

$$r = \frac{1}{n-1} \sum_{i=1}^{n} \left(\frac{X_i - \bar{X}}{s_X}\right)\left(\frac{Y_i - \bar{Y}}{s_Y}\right) \quad (3)$$

where X and Y may be waveforms of electroencephalogram signals in two channels, n is the number of correlation statistical sample points, $s_X$ is the standard deviation of X, $s_Y$ is the standard deviation of Y, $\bar{X}$ is the expectation of X, and $\bar{Y}$ is the expectation of Y. The range of r is [−1, 1], where −1 represents the completely negative correlation, and 1 represents the completely positive correlation.

In one embodiment, the determination module 20 may acquire the anesthesia stage at which the patient may be located according to the high-frequency energy obtained by the energy calculation unit and the numerical value of the correlation between the electroencephalogram signals in the two channels that may be obtained by the correlation calculation unit.

In one embodiment, under different anesthesia stage conditions, the high-frequency energy may be different, and the correlation between the electroencephalogram signals in the two channels may be also different. The determination module 20 can monitor the anesthesia stage according to the high-frequency energy and the correlation. However, this embodiment may be not limited thereto. For example, the determination module 20 may also monitor the anesthesia stage according to other types of characteristics, such as complexity or entropy among the nonlinear-domain characteristics.

In one embodiment, the determination module 20 can determine whether the high-frequency energy is high or low. Whether the high-frequency energy is high or low (that is, whether the electromyogram level is high or low) can be determined according to the high-frequency energy and a first threshold. The high-frequency energy may be obtained by the energy calculation unit.

In one embodiment, the first threshold may be an empirical threshold. The empirical threshold may be an energy threshold that may be summarized by a doctor during a large number of surgical procedures and used to distinguish electromyogram interference signals of a patient at different anesthesia stages.

In one embodiment, the first threshold may also be an adaptive threshold. The adaptive threshold of the energy of the electromyogram interference signal may be related to the level of the high-frequency energy. The initial value of the adaptive threshold may be set as an empirical threshold. As the energy level of the electromyogram interference signal changes during a surgical procedure, the numerical value of the adaptive threshold may also change. As a result, the first threshold can be adjusted in a timely manner according to the real-time energy level of the electromyogram interference signal, to determine the anesthesia stage more accurately.

In one embodiment, if the energy of the electromyogram interference signal is greater than or equal to the first threshold, the level of the high-frequency energy is high, and the anesthesia stage can be determined to be the lucid interval. If the energy of the electromyogram interference signal is less than the first threshold, the level of the high-frequency energy is low, and the anesthesia stage can be determined to be the anesthesia period. As a result, the determination module 20 can preliminarily determine the monitored anesthesia stage of the patient according to the first threshold and the energy of the electromyogram interference signal.

In one embodiment, whether the correlation is positive or negative may be related to the determination of the anesthesia stage. There may be usually an error in determining the anesthesia stage only by means of the sign of the numerical value of the correlation. This may be due to the fact that for the numerical value around zero, the anesthesia stage at which the patient may be located usually cannot be accurately determined only by means of the sign thereof.

In one embodiment, whether the correlation is positive or negative may need to be determined by comparing the numerical value of the correlation with a second threshold and a third threshold. Specifically, in the determination module 20, if the Pearson correlation coefficient is greater than or equal to the second threshold, the correlation may be determined to be a positive correlation. If the Pearson correlation coefficient is less than or equal to the third threshold, the correlation may be determined to be a negative correlation. The second threshold may be a positive number greater than zero. The third threshold may be a negative number less than zero.

In addition, in one embodiment, the determination module 20 can monitor the different anesthesia stages by combining the determination of whether the energy of the electromyogram interference signal is high or low and the determination of whether the numerical value of the correlation is positive or negative.

In one embodiment, if the determination module 20 determines that the energy of the electromyogram (EMG) interference signal is high, and the determination module 20 may determine that the correlation is negative, that is, the electroencephalogram signals in the two channels may be negatively correlated, then the determination module 20 determines that the anesthesia stage may be the lucid interval.

In one embodiment, if the determination module 20 determines that the energy of the electromyogram interference signal is low, and the determination module 20 may determine that the correlation is positive, that is, the electroencephalogram signals in the two channels may be positively correlated, then the determination module 20 determines that the anesthesia stage may be a stable stage.

In one embodiment, if the determination module 20 determines that the patient is in the lucid interval, the determination module 20 may determine that the energy of the electromyogram interference signal changes from high to low, and the determination module 20 determines that the correlation may be positive, that is, the electroencephalogram signals in the two channels may be positively correlated, then the determination module 20 determines that the anesthesia stage at which the patient is located may be the induction stage.

In one embodiment, if the determination module 20 determines that the patient is in the stable stage, the determination module 20 may determine that the energy of the electromyogram interference signal changes from low to high, and the determination module 20 may determine that the correlation is negative, that is, the electroencephalogram signals in the two channels may be negatively correlated, then the determination module 20 determines that the anesthesia stage at which the patient may be located can be a recovery stage. As a result, the determination module 20 can more accurately determine the anesthesia stage using the comprehensive determination of the correlation and the energy level of the electromyogram interference signal.

In one embodiment, as shown in FIG. 4, the anesthesia depth calculation device 1 may further include the selection module 30. The selection module 30 may determine an anesthesia depth calculation strategy according to the anesthesia stage at which the patient may be located. Specifically, the selection module 30 may determine the anesthesia depth calculation strategy by receiving the anesthesia stage at which the patient may be located that can be obtained by the determination module 20. The selection module 30 may be a processor such as a central processing unit (CPU), a microprocessor unit (MPU), or an application specific integrated circuit (ASIC).

In one embodiment, the anesthesia depth calculation strategy may include at least a first calculation strategy and a second calculation strategy. The first calculation strategy may be to calculate the anesthesia depth with a relatively short signal, and the second calculation strategy may be to calculate the anesthesia depth with a longer signal than in the first calculation strategy. That is, compared with the electroencephalogram signal collected for the second calculation strategy, the electroencephalogram signal collected for the first calculation strategy may have a shorter sampling time or a shorter signal length. For example, if a set collection time for the electroencephalogram signal collected for the first calculation strategy may be 5 seconds, a set collection time for the electroencephalogram signal collected for the second calculation strategy may be a time greater than 5 seconds, such as 10 seconds, or 20 seconds.

In one embodiment, when the patient may be in the induction stage, the selection module 30 may use the first calculation strategy. When the patient may be in the other periods, the selection module 30 may use the second calculation strategy. The response speed at which the anesthesia depth may be calculated by using the first calculation strategy may be faster than the response speed at which the anesthesia depth may be calculated by using the second calculation strategy.

Of course, it is also possible that when the patient is in the induction stage or in the recovery stage, the selection module 30 may use the first calculation strategy. When the patient is in the lucid interval or in the stable stage, the selection module 30 may use the second calculation strategy. The calculation strategy can be selected according to actual requirements.

In one embodiment, as shown in FIG. 4, the anesthesia depth calculation device 1 may further include the calculation module 40. The calculation module 40 may calculate an anesthesia depth in a corresponding time period according to the determined anesthesia depth calculation strategy. In some examples, the calculation module 40 may be a processor such as a central processing unit (CPU), a microprocessor unit (MPU), or an application specific integrated circuit (ASIC).

In one embodiment, the calculation module 40 may calculate the anesthesia depth in the corresponding time period using the electroencephalogram signal in the corresponding time period, according to the anesthesia depth calculation strategy determined by the selection module 30.

In one embodiment, the electroencephalogram signal may be subjected to characteristic extraction to obtain different characteristics. The extracted characteristics may be at least one of time-domain characteristics, frequency-domain characteristics, and complex-domain characteristics. The calculation module 40 may calculate, according to the extracted signal characteristics, the anesthesia depth value in the case of the corresponding characteristics. That is, the calculation module 40 may calculate the anesthesia depth in the corresponding time period according to the signal characteristics of the electroencephalogram signal in the corresponding time period.

Figure 5:
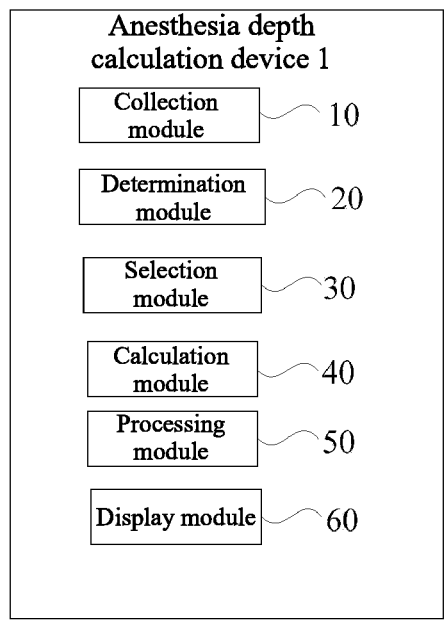
FIG. 5 is a block diagram showing modules of another anesthesia depth calculation device according to an embodiment of this disclosure.

FIG. 5 is a block diagram showing modules of another anesthesia depth calculation device according to an embodiment.

In one embodiment, as shown in FIG. 5, the anesthesia depth calculation device 1 may further include a processing module 50. The processing module 50 may perform related processing on the collected electroencephalogram signal. Specifically, if it is monitored by the processing module 50 that the anesthesia stage may be the lucid interval or the patient may enter the recovery stage (also referred to as the anesthesia recovery stage) from the stable stage, low-frequency interference detection and high-pass filtering may be performed on the electroencephalogram signal. As a result, the eye movement interference signal may be filtered out, and an abnormal falling in the lucid interval may be avoided, such that the anesthesia depth may be kept stable.

In one embodiment, if it is monitored by the processing module 50 that the anesthesia stage may be in the induction stage or the patient may enter the induction stage (also referred to as the anesthesia induction stage) from the lucid interval, the low-frequency interference detection and high-pass filtering performed on the electroencephalogram signal may be stopped. The frequency of low-frequency interference is generally 0 to 10 Hz, and the threshold of high-pass filtering may be greater than or equal to 2 Hz. As a result, the smoothing length of the anesthesia depth value can be reduced, so that the electroencephalogram signal in the induction stage can be used to calculate the anesthesia depth, so as to achieve the purpose of fast response.

In one embodiment, as shown in FIG. 5, the anesthesia depth calculation device 1 may further include a display module 60.

In one embodiment, the display module 60 may receive the anesthesia depth value calculated by the calculation module 40 and display a display value of the anesthesia depth value. As a result, the anesthesia depth value can be directly read.

In one embodiment, the electroencephalogram signal may be first obtained by the collection module 10, and the determination module 20 may obtain the anesthesia stage at which the patient may be located according to the collected electroencephalogram signal. The selection module 30 may select the anesthesia depth calculation strategy according to the anesthesia stage, and the calculation module 40 may obtain the anesthesia depth value for the corresponding calculation strategy. As a result, as shown in FIG. 3, it is possible to accurately determine the anesthesia stage, and resolve the problems of abnormal falling during the lucid interval (the possibility of abnormal falling in the segment M being reduced) and slow response speed during the induction stage (the anesthesia depth having a decreasing trend from the initial point of the segment N) caused by the misjudgment.

Hereinafter, an anesthesia stage identification method according to an embodiment will be described in detail with reference to FIG. 6.

Figure 6:
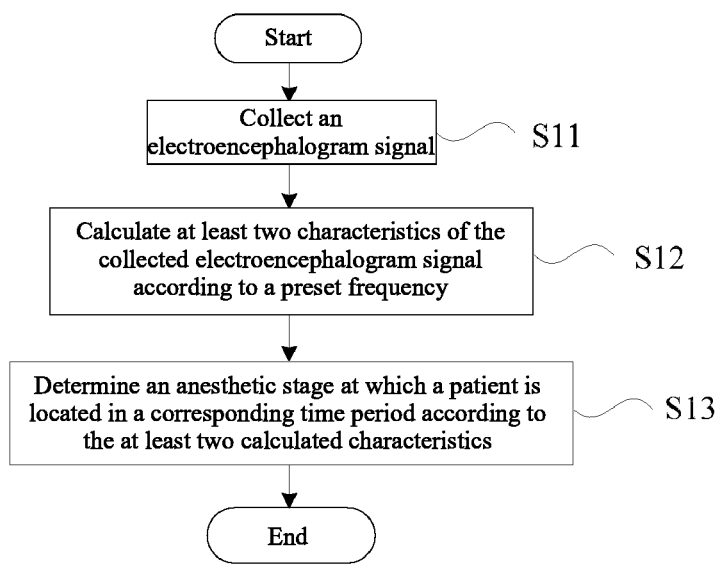
FIG. 6 is a flowchart showing an anesthesia stage identification method according to an embodiment of this disclosure.

FIG. 6 is a flowchart showing an anesthesia stage identification method according to this embodiment.

In one embodiment, as shown in FIG. 6, the anesthesia stage identification method may include: collecting an electroencephalogram signal (step S11); calculate at least two characteristics of the collected electroencephalogram signal according to a preset frequency (step S12); and determining an anesthesia stage at which a patient may be located in a corresponding time period according to the at least two calculated characteristics (step S13).

In step S11, the collected electroencephalogram signal may include electroencephalogram signals of at least two channels. That is, at least two different positions of the head of a patient may be selected to collect the electroencephalogram signals. For example, it is possible to collect electroencephalogram signals of three channels, for example, it is possible to select an area around the human eye to collect an electroencephalogram signal, to select an area where the cerebral cortex of the patient may be located to collect an electroencephalogram signal, and to select an area around an ear of the patient to collect an electroencephalogram signal.

In one embodiment, the electroencephalogram signal may be collected by means of a sensor. For example, the electroencephalogram signal may be collected by means of electrode pads.

In one embodiment, the anesthesia stage identification method may further include calculating at least two characteristics of the collected electroencephalogram signal according to a preset frequency (step S12).

In step S12, the at least two characteristics of the electroencephalogram signal may be a correlation between the electroencephalogram signals of any two of the channels, and an electromyogram (EMG) level obtained from a high-frequency energy in the electroencephalogram signal of any one of the channels. Of course, it can also be implemented by means of other characteristics, for example, nonlinear characteristics, such as complexity or entropy.

In one embodiment, the high-frequency energy may be different at different anesthesia stages. In step S12, the high-frequency energy may be quantified using a power spectral density. First, a Fourier transform may be performed on the electromyogram interference signal, and then the Parseval's theorem may be used to obtain the power spectral density. As a result, the energy of the electromyogram interference signal can be obtained.

In one embodiment, step S12 may further include selecting two channels from the multiple channels, and calculating a correlation between the electroencephalogram signals in the two channels.

In some examples, in step S12, among the electroencephalogram signals of the two selected channels, the electroencephalogram signal of one channel may include an eye movement interference signal, and the electroencephalogram signal of the other channel may not include any eye movement interference signal. For example, an area around the eye may be selected to collect the electroencephalogram signal of one channel, and an area away from the eye, such as a brain scalp area, may be selected to collect the electroencephalogram signal of the other channel.

In addition, in one embodiment, the correlation may be calculated by means of a Pearson correlation coefficient, that is, the correlation may be calibrated by means of the Pearson correlation coefficient. The Pearson correlation coefficient may be used to measure the linear relationship between the electroencephalogram signals in the two channels. As a result, the correlation between the electroencephalogram signals can be obtained.

In one embodiment, the anesthesia stage identification method may further involve determining the anesthesia stage at which the patient may be located in a corresponding time period according to the at least two calculated characteristics (step S13).

In step S13, the at least two characteristics of the electroencephalogram signal may be a correlation between the electroencephalogram signals of any two of the channels, and a high-frequency energy in the electroencephalogram signal of any one of the channels. As a result, it is possible to determine the anesthesia stage at which the patient may be located in the corresponding time period from the obtained high-frequency energy, and the correlation between the electroencephalogram signals of any two of the channels or changes in the correlation.

In one embodiment, whether the high-frequency energy is high or low can be determined by comparing the energy of the electromyogram interference signal calculated in step S12 with a first threshold. As a result, whether the high-frequency energy is high or low can be accurately obtained, and the anesthesia stage at which the patient may be located can be determined more accurately.

In one embodiment, the first threshold may be an empirical threshold. The empirical threshold may be a threshold that is summarized by a doctor based on a large amount of surgical experience and used to distinguish the high-frequency energies of a patient at different anesthesia stages.

In one embodiment, the first threshold may also be an adaptive threshold. The adaptive threshold of the energy of the electromyogram interference signal may be related to the level of the high-frequency energy. The initial value of the adaptive threshold may be set as an empirical threshold. As the energy level of the electromyogram interference signal may change during a surgical procedure, the numerical value of the adaptive threshold also may change. As a result, the first threshold can be adjusted in a timely manner according to the real-time energy level of the electromyogram interference signal, to determine the anesthesia stage more accurately.

In one embodiment, if the energy of the electromyogram interference signal is greater than or equal to the first threshold, the level of the high-frequency energy may be high, and the anesthesia stage may be the lucid interval. If the energy of the electromyogram interference signal is less than the first threshold, the level of the high-frequency energy may be low, and the anesthesia stage may be the anesthesia period. As a result, it is possible to preliminarily determine the monitored anesthesia stage of the patient according to the first threshold and the energy of the electromyogram interference signal.

In one embodiment, whether the correlation is positive or negative may need to be determined by comparing the numerical value of the correlation with a second threshold and a third threshold. Specifically, if the Pearson correlation coefficient is greater than or equal to the second threshold, the correlation may be determined to be a positive correlation. If the Pearson correlation coefficient is less than or equal to the third threshold, the correlation may be determined to be a negative correlation. The second threshold may be a positive number greater than zero. The third threshold may be a negative number less than zero. The correlation determined according to the second threshold and the third threshold can determine the anesthesia stage more accurately. As a result, the relationship between the correlation and the anesthesia stage may be more accurate, and the anesthesia stage can be determined more accurately.

In one embodiment, the anesthesia stage may be divided into a lucid interval, an induction stage, a stable stage and a recovery stage. In step S13, if the energy of the electromyogram interference signal is determined to be high, and the correlation may be negative correlation, that is, the electroencephalogram signals in the two channels may be negatively correlated, then the anesthesia stage may be determined to be the lucid interval. If the energy of the electromyogram interference signal is determined to be low, and the correlation may be determined to be positive, that is, the electroencephalogram signals in the two channels may be positively correlated, then the anesthesia stage may be determined to be the stable stage.

In one embodiment, if the patient is determined to be in the lucid interval, the energy of the electromyogram interference signal may be determined to be from high to low, and the correlation may be determined to be positive, that is, the electroencephalogram signals in the two channels may be positively correlated, then the anesthesia stage at which the patient may be located can be determined to be the induction stage.

In one embodiment, if the patient is determined to be in the stable stage, the energy of the electromyogram interference signal may be determined to be from low to high, and the correlation may be determined to be negative, that is, the electroencephalogram signals in the two channels may be negatively correlated, then the anesthesia stage at which the patient may be located can be determined to be the recovery stage. As a result, in the lucid interval and in the induction stage, the correlation between the electroencephalogram signals of different channels may be different. The anesthesia stage at which the patient may be located can be determined more accurately by means of the comprehensive determination of the correlation and the energy level of the electromyogram interference signal.

In this case, the anesthesia stage at which the patient may be located can be obtained more accurately according to the high-frequency energy and the correlation or changes in the correlation.

In addition, the anesthesia stage may be divided into a lucid interval, an induction stage, a stable stage and a recovery stage. As a result, which one of the lucid interval, the induction stage, the stable stage and the recovery stage in which the patient may be located can be obtained more accurately according to the high-frequency energy and the correlation or changes in the correlation.

Hereinafter, anesthesia depth calculation methods according to embodiments will be described in detail with reference to FIG. 7 and FIG. 8.

Figure 7:
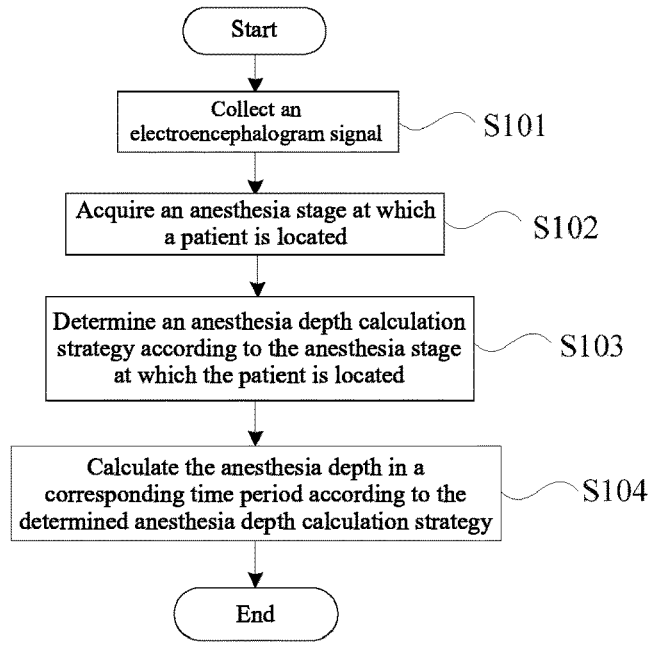
FIG. 7 is a flowchart showing an anesthesia depth calculation method according to an embodiment of this disclosure.

FIG. 7 is a flowchart showing an anesthesia depth calculation method according to an embodiment. FIG. 8 is a flowchart showing another anesthesia depth calculation method according to an embodiment.

In one embodiment, as shown in FIG. 7, the anesthesia depth calculation method may include collecting an electroencephalogram signal (step S101). Here, step S101 is similar to step S11.

In one embodiment, the electroencephalogram signal may be collected by means of a sensor. For example, the electroencephalogram signal may be collected by means of electrode pads (see step S11 described above).

In one embodiment, signals may be collected by means of three electrode pads, one of which may be a common electrode pad, namely, an R electrode pad, and the other two electrode pads may be a T electrode pad and an E electrode pad. The electroencephalogram signals of the two channels can be obtained by means of the potential differences between the T and E electrode pads and the R electrode pad, respectively.

In step S101, electroencephalogram signals of multiple channels can be collected, that is, collection may be performed on at least two different positions of the head of the patient. The positions where the electroencephalogram signals may be collected may be in different areas of the head of the patient, or may be different positions in the same area.

In one embodiment, as shown in FIG. 7, the anesthesia depth calculation method may further include acquiring an anesthesia stage at which the patient may be located (step S102). As mentioned above, the anesthesia stage may be divided into a lucid interval, an induction stage, a stable stage and a recovery stage. Since different anesthesia stages represent different stages, the determination of the anesthesia stage at which the patient may be located can provide a basis for the subsequent determination of an anesthesia depth calculation strategy.

In step S102, the collected electroencephalogram signal may be used to calculate at least two characteristics of the electroencephalogram signal. The anesthesia stage at which the patient may be located in a corresponding time period may be determined according to the at least two characteristics. That is, it is possible to automatically identify, according to the collected electroencephalogram signal, the anesthesia stage at which the patient may be located in the case of the corresponding electroencephalogram signal. As a result, the anesthesia stage at which the patient may be located can be obtained more efficiently.

In one embodiment, for automatically identifying the anesthesia stage at which the patient may be located in the case of the corresponding electroencephalogram signal (that is, the anesthesia stage identification method), reference can be made to the anesthesia stage identification method described above.

In one embodiment, as shown in FIG. 7, the anesthesia depth calculation method may further include determining an anesthesia depth calculation strategy according to the anesthesia stage at which the patient may be located (step S103).

In one embodiment, the anesthesia stage can be obtained in step S102. Since the anesthesia stage may be different, the calculation strategy selected in step S103 may be also different accordingly.

In one embodiment, the anesthesia depth calculation strategy may include at least a first calculation strategy and a second calculation strategy. The first calculation strategy may be to calculate the anesthesia depth with a relatively short signal, and the second calculation strategy may be to calculate the anesthesia depth with a longer signal than in the first calculation strategy. That is, compared with the electroencephalogram signal collected for the second calculation strategy, the electroencephalogram signal collected for the first calculation strategy may have a shorter sampling time or a shorter signal length. As a result, the anesthesia depth value can be obtained according to different calculation strategies.

In step S103, the response speed at which the anesthesia depth may be calculated by using the first calculation strategy may be faster than the response speed at which the anesthesia depth may be calculated by using the second calculation strategy. When the patient may be in the induction stage or in the recovery stage, the first calculation strategy may be used. When the patient may be in the lucid interval or in the stable stage, the second calculation strategy may be used. As a result, a faster anesthesia depth response speed can be obtained.

In one embodiment, as shown in FIG. 7, the anesthesia depth calculation method may further include calculating an anesthesia depth in a corresponding time period according to the determined anesthesia depth calculation strategy (step S104). In this case, the anesthesia depth value can be obtained more accurately and quickly.

In step S104, the electroencephalogram signal under the selected calculation strategy may be acquired according to the anesthesia depth calculation strategy determined in step S103. Related processing may be then performed on the obtained electroencephalogram signal.

In step S104, when it is monitored that the anesthesia stage may be in the lucid interval or the patient enters the recovery stage (also referred to as the anesthesia recovery stage) from the stable stage, low-frequency interference detection and high-pass filtering may be performed on the electroencephalogram signal; and when it is monitored that the anesthesia stage may be in the induction stage or the patient enters the induction stage (also referred to as the anesthesia induction stage) from the lucid interval, the low-frequency interference detection and high-pass filtering performed on the electroencephalogram signal may be stopped.

In one embodiment, the eye movement interference signal can be filtered out by performing low-frequency interference detection and high-pass filtering on the electroencephalogram signals in the lucid interval, avoiding an abnormal falling in the lucid interval, such that the anesthesia depth may be kept stable. Stopping the low-frequency interference detection and high-pass filtering performed on the electroencephalogram signal in the induction stage can reduce the smoothing length of the anesthesia depth value, so that the electroencephalogram signal in the induction stage can be used to calculate the anesthesia depth, so as to achieve the purpose of fast response.

In step S104, it may further include performing characteristic extraction on the filtered electroencephalogram signal to calculate the anesthesia depth value. The extracted characteristic may be a time-domain characteristic, a frequency-domain characteristic, or at least one of complex-domain characteristics. The anesthesia depth value may be calculated according to the extracted characteristic.

Figure 8:
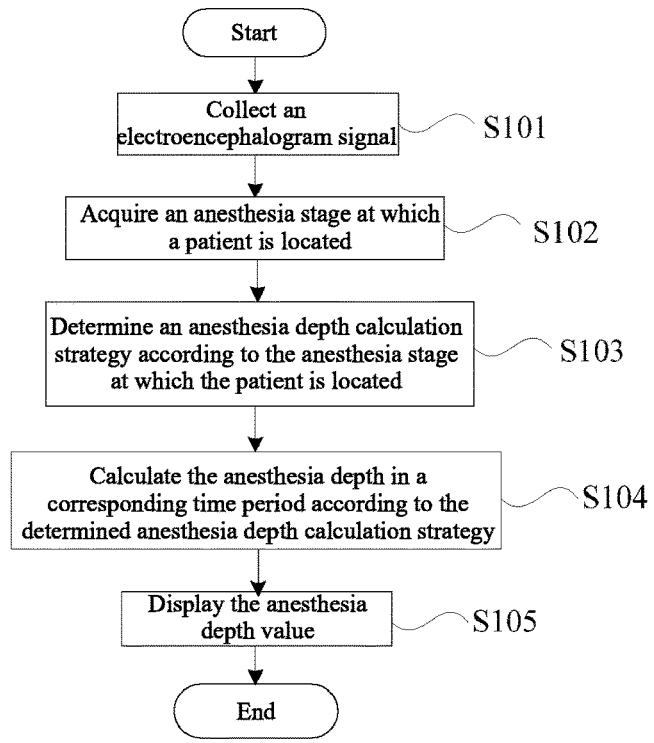
FIG. 8 is a flowchart showing another anesthesia depth calculation method according to an embodiment of this disclosure.

In one embodiment, as shown in FIG. 8, the anesthesia depth calculation method may include displaying the anesthesia depth value (step S105). By means of step S105, the anesthesia depth value of the patient can be obtained intuitively.

In one embodiment, in the anesthesia depth calculation method, the anesthesia stage may be monitored by calculating the energy of the electromyogram interference signal and calculating the correlation between the electroencephalogram signals in the two channels. In this case, in combination with the energy of the electromyogram interference signal and the correlation between the electroencephalogram signals in the two channels, it is possible to accurately obtain the anesthesia stage at which the patient may be located, and to resolve the problems of abnormal falling during a lucid interval and slow response speed during an induction stage caused by misjudgment. In addition, different calculation strategies can be adjusted at different anesthesia stages, so as to obtain different calculation strategies for the outgoing value at different anesthesia stages, to meet the clinical requirements for different anesthesia stages.

In one embodiment, the acquisition of the anesthesia depth value may be not limited to the method described above. For example, there may be the following modified anesthesia stage monitoring methods.

In one embodiment, the difference from the above anesthesia depth calculation method may be that after step S101 and step S102 may be performed, step S104 may use the first calculation strategy and the second calculation strategy to perform signal characteristic extraction on the electroencephalogram signal and calculate the anesthesia depth in parallel. When the patient may be in the induction stage or in the anesthesia recovery stage, step S103 may use the calculation result of the first calculation strategy as the anesthesia depth at the corresponding stage. When the patient may be in the lucid interval or the anesthesia stable stage, step S103 may use the calculation result of the second calculation strategy as the anesthesia depth at the corresponding stage. Then, by means of step S105, the anesthesia depth value may be displayed. As a result, it is possible to respond to the anesthesia depth more quickly.

Hereinafter, steps in some examples of anesthesia depth calculation methods according to embodiments will be described in detail with reference to FIGS. 9 and 10.

Figure 9:
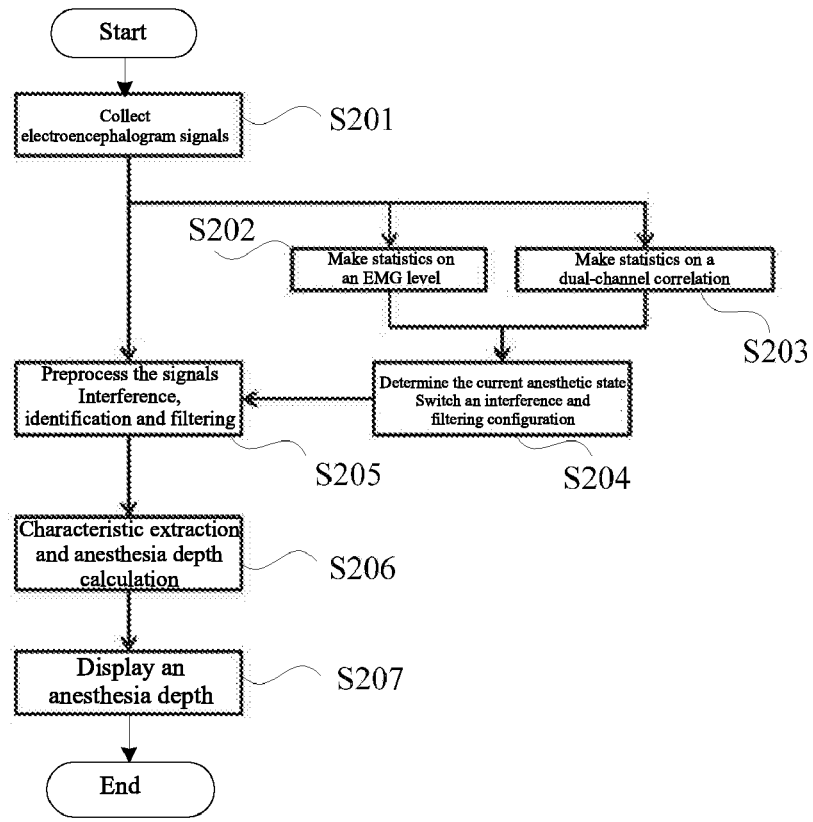
FIG. 9 is a flowchart showing an anesthesia depth calculation method according to an embodiment of this disclosure.

FIG. 9 is a flowchart showing an anesthesia depth calculation method according to an embodiment. FIG. 10 is a flowchart showing another anesthesia depth calculation method according to an embodiment.

In some examples, as shown in FIG. 9, the anesthesia depth calculation method may include collecting electroencephalogram signals (step S201). Here, step S201 is similar to step S101.

In one embodiment, as shown in FIG. 9, the anesthesia depth calculation method may further include making statistics on high-frequency energies of the collected electroencephalogram signals (step S202) and making statistics on a dual-channel correlation between the collected electroencephalogram signals (step S203). For the method for calculating the high-frequency energies and the dual-channel correlation, reference is made to step S12.

In addition, the anesthesia depth calculation method may further include determining the anesthesia stage according to the high-frequency energies and the dual-channel correlation, selecting a calculation strategy, and selecting an interference and filtering configuration (step S204). For the determination of the anesthesia stage, reference may be made to step S13. For the selection of the calculation strategy, reference can be made to step S103.

In addition, the anesthesia depth calculation method may further include preprocessing the collected electroencephalogram signals according to the selected interference and filtering configuration (step S205). Characteristic extraction and anesthesia depth calculation may be performed on the preprocessed electroencephalogram signals (step S206). In step S205, when it is monitored that the anesthesia stage may be the lucid interval or the patient may enter the recovery stage (also referred to as the anesthesia recovery stage) from the stable stage, low-frequency interference detection and high-pass filtering may be performed on the electroencephalogram signals. The specific processing may be as described above and will not be repeated here. For step S206, reference can be made to step S104. The anesthesia depth may be displayed (step S207). Step S207 may be similar to step S105.

Figure 10:
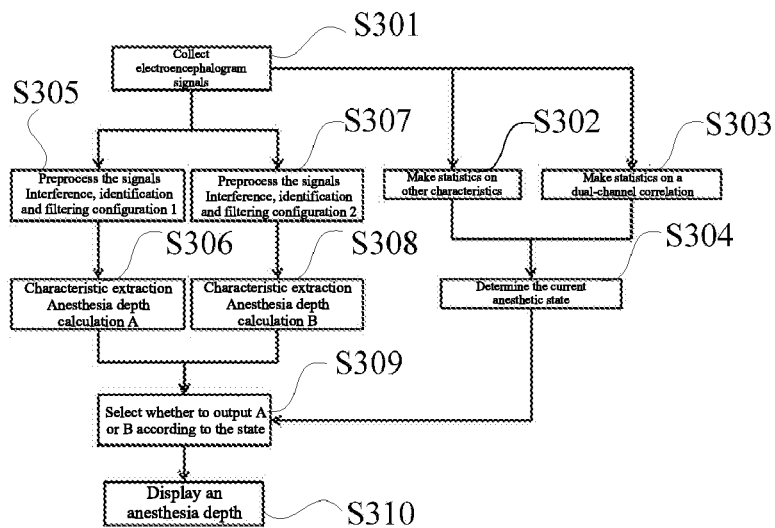
FIG. 10 is a flowchart showing another anesthesia depth calculation method according to an embodiment of this disclosure.

In some examples, as shown in FIG. 10, the anesthesia depth calculation method may include collecting electroencephalogram signals (step S301). Here, step S301 is similar to step S101.

In one embodiment, as shown in FIG. 10, the anesthesia depth calculation method may further include making statistics on other characteristics of the collected electroencephalogram signals (step S302) and making statistics on the dual-channel correlation between the collected electroencephalogram signals (step S303). For the method for calculating the dual-channel correlation, reference may be made to step S12. The other characteristics may be selected from time-domain characteristics, frequency-domain characteristics, and/or nonlinear-domain characteristics.

In addition, the anesthesia depth calculation method may further include determining the anesthesia stage according to the other characteristics and the dual-channel correlation (step S304).

In addition, the anesthesia depth calculation method may further include preprocessing the collected electroencephalogram signals by means of a first interference and filtering configuration (step S305), and performing characteristic extraction on the preprocessed electroencephalogram signals and calculating a first anesthesia depth thereof (step S306); and preprocessing the collected electroencephalogram signals by means of a second interference and filtering configuration (step S307), and performing characteristic extraction on the preprocessed electroencephalogram signals and calculating a second anesthesia depth thereof (step S308).

In step S305, the first interference and filtering configuration may be an interference and filtering device for performing low-frequency interference detection and high-pass filtering on the electroencephalogram signals in the lucid interval. In step S306, the first anesthesia depth may be an anesthesia depth value corresponding to the electroencephalogram signals passing through the first interference and filtering configuration. In step S307, the second interference and filtering configuration may be an interference and filtering device for stopping the low-frequency interference detection and high-pass filtering performed on the electroencephalogram signals in the induction stage. The second anesthesia depth may be an anesthesia depth value corresponding to the electroencephalogram signals passing through the second interference and filtering configuration. However, this embodiment may be not limited thereto. The first interference and filtering configuration, and the first anesthesia depth may be further used to preprocess the electroencephalogram signals and calculate the anesthesia depth thereof in the induction stage. Correspondingly, the second interference and filtering configuration, and the second anesthesia depth may be further used to preprocess the electroencephalogram signals and calculate the anesthesia depth thereof in the lucid interval.

In addition, the anesthesia depth calculation method may further include selecting the first anesthesia depth or the second anesthesia depth according to the anesthesia stage in step S304 (step S309). The anesthesia depth may be displayed (step S310). Step S310 may be similar to step S105.

Although this disclosure is described above in detail with reference to the accompanying drawings and the embodiments. However, it may be understood that the foregoing description does not limit this disclosure in any form. A person skilled in the art may make variations and changes to this disclosure as required without departing from the essence, spirit, and scope of this disclosure. All these variations and changes fall within the scope of this disclosure.

What is claimed is:

1. A method for identifying an anesthesia stage a patient is at, comprising:
   collecting an electroencephalogram signal comprising electroencephalogram signals of at least two channels;
   calculating a correlation between the electroencephalogram signals of any two of the channels and a high-frequency energy in an electroencephalogram signal of any one of the channels; and
   determining the anesthesia stage in a corresponding time period based on the high-frequency energy and the correlation between the electroencephalogram signals, which comprises:
   determining the anesthesia stage in the corresponding time period according to the high frequency energy and the correlation between the electroencephalogram signals of any two of the channels or according to the high-frequency energy and changes in the correlation between the electroencephalogram signals of any two of the channels.

2. The method of claim 1, wherein the anesthesia stage is one of a lucid interval, an induction stage, a stable stage or a recovery stage.

3. The method of claim 2, wherein determining the anesthesia stage further comprises:
when the high-frequency energy is high and the correlation is negative, determining the anesthesia stage to be the lucid interval;
when the high-frequency energy is low and the correlation is positive, determining the anesthesia stage to be the stable stage;
when the patient is in the lucid interval, determining that the patient enters into the induction stage as the high-frequency energy changes from high to low, and the correlation becomes positive; and
when the patient is in the stable stage, determining the patient enters into the recovery stage as the high-frequency energy changes from low to high, and the correlation becomes negative.

4. The method of claim 1, further comprising:
comparing the high-frequency energy with a first threshold to determine whether the high-frequency energy is high or low.

5. The method of claim 4, wherein the first threshold is an adaptive threshold related to the high-frequency energy.

6. The method of claim 1, wherein the correlation is calibrated by a Pearson correlation coefficient.

7. The method of claim 6, wherein
when the Pearson correlation coefficient is greater than or equal to a second threshold, the correlation is a positive correlation; and
when the Pearson correlation coefficient is less than or equal to a third threshold, the correlation is a negative correlation.

8. A method for calculating an anesthesia depth, comprising:
collecting an electroencephalogram signal;
acquiring an anesthesia stage a patient is at;
determining a strategy for calculating an anesthesia depth according to the anesthesia stage, different strategies corresponding to different response speeds at which the anesthesia depth is calculated; and
calculating the anesthesia depth in a time period corresponding to the anesthesia stage using the determined strategy.

9. The method of claim 8, wherein the determined strategy comprises at least a first strategy or a second strategy.

10. The method of claim 9, wherein a response speed at which the anesthesia depth is calculated by using the first strategy is faster than a response speed at which the anesthesia depth is calculated by using the second strategy,
wherein calculating the anesthesia depth in the time period corresponding to the anesthesia stage using the determined strategy comprises:
using the first strategy when the patient is at an induction stage.

11. The method of claim 10, wherein
the first strategy comprises calculating the anesthesia depth with a relatively short signal, and the second strategy comprises calculating the anesthesia depth with a longer signal than that used in the first strategy.

12. The method of claim 9, wherein calculating the anesthesia depth in the time period corresponding to the anesthesia stage using the determined strategy comprises:
using the first strategy and the second strategy to calculate the anesthesia depth in parallel; and
setting, when the patient is at an induction stage, a calculation result of the first strategy as the anesthesia depth.

13. The method of claim 8, wherein acquiring the anesthesia stage comprising:
calculating at least two characteristics of the collected electroencephalogram signal; and
determining the anesthesia stage in the corresponding time period according to the two characteristics.

14. An anesthesia device, comprises:
a sensor that collects an electroencephalogram signal;
a memory that stores the collected electroencephalogram signal comprising electroencephalogram signals of at least two channels; and
a processor that is configured to:
calculate correlation between the electroencephalogram signals of any two of the channels and a high-frequency energy in an electroencephalogram signal of any one of the channels; and
determine an anesthesia stage at which a patient is in a corresponding time period based on the high-frequency energy and the correlation between the electroencephalogram signals of any two of the channels or according to the high-frequency energy and changes in the correlation between the electroencephalogram signals of any two of the channels.

15. The device of claim 14, wherein
the processor is further configured to compare the high-frequency energy with a first threshold to determine whether the high-frequency energy is high or low; and
the first threshold is an adaptive threshold related to the high-frequency energy.

16. The device of claim 15, wherein the correlation is calibrated by a Pearson correlation coefficient.

17. The device of claim 15, wherein the processor is further configured to:
determine a strategy to calculate an anesthesia depth according to the anesthesia stage, different strategies corresponding to different response speeds at which the anesthesia depth is calculated; and
calculate the anesthesia depth in the corresponding time period according to the determined strategy for the anesthesia depth calculation.

* * * * *